United States Patent [19]

Nowacki et al.

[11] Patent Number: 4,534,343

[45] Date of Patent: Aug. 13, 1985

[54] METERED DOSE INHALER

[75] Inventors: Christopher Nowacki, Arlington Heights; Alfred G. Brisson, Schaumburg, both of Ill.

[73] Assignee: Trutek Research, Inc., Arlington Heights, Ill.

[21] Appl. No.: 574,340

[22] Filed: Jan. 27, 1984

[51] Int. Cl.³ .......................................... A61M 15/00
[52] U.S. Cl. .......................... 128/200.23; 128/203.15
[58] Field of Search .................... 128/200.23, 200.21, 128/200.18, 203.15, 726; 604/24, 26, 58, 77

[56] References Cited

U.S. PATENT DOCUMENTS

| | | | |
|---|---|---|---|
| 2,788,784 | 4/1957 | Birch et al. | 128/200.23 |
| 3,897,779 | 8/1975 | Hansen | 128/203.15 |
| 4,174,712 | 11/1979 | Moren et al. | 128/200.18 |
| 4,253,468 | 3/1981 | Lehmbeck | 128/200.21 |

FOREIGN PATENT DOCUMENTS

| | | | |
|---|---|---|---|
| 513678 | 11/1920 | France | 128/200.21 |
| 79918 | 1/1963 | France | 128/200.23 |
| 975754 | 11/1964 | United Kingdom | 128/200.23 |
| 2000555 | 1/1979 | United Kingdom | 128/200.23 |

Primary Examiner—Henry J. Recla
Attorney, Agent, or Firm—Trexler, Bushnell & Wolters, Ltd.

[57] ABSTRACT

A metered dose inhaler is provided for inhalation of asthmatic medication. An upright cylindrical air chamber has structure at the top for receiving a pressurized canister of asthmatic medication and for conducting metered doses thereof into the air chamber. A one way valve is provided at the bottom of the air chamber to admit air but to preclude escape of mist. A mouthpipe is provided at the top of the chamber on one side thereof for insertion in a patient's mouth. A deflectable diaphragm is provided in cooperation with the mouthpipe so that when a patient inhales the diaphragm deflects to permit the mist in the air chamber to be inhaled, air entering the one way valve of the bottom of the air chamber to supplant the mist. When the patient exhales the diaphragm closes, and the exhaled air is bypassed to the outside.

9 Claims, 7 Drawing Figures

METERED DOSE INHALER

RELATED APPLICATION

The present application is related to and forms an improvement over our co-pending application Ser. No. 359,679, filed Mar. 19, 1982 and now U.S. Pat. No. 4,470,412 for "Inhalation Valve" assigned to the same assignee, Trutek Research, Inc. of Arlington Heights, Illinois.

BACKGROUND OF THE INVENTION

A person suffering from asthma may when suffering an asthmatic attack have rather considerable trouble in breathing, due to swelling in the bronchi and due to secretion of mucus. There are various antiasthmatic pills that are effective, but which generally are somewhat slow-acting. There are also medications available for intravenous treatment which work quite rapidly, but which require administration by skilled medical personnel. For most patients the promptest, immediately available relief is by way of an inhalant. Epinephrine or other suitable asthmatic medication is packaged with a suitable diluent in a small pressurized cannister or cartridge which interfits with a mouthpiece. The patient places the mouthpiece in his mouth, and depresses the cartridge, thereby releasing a measured amount of medication which is inhaled through the mouthpiece.

Some patients do not inhale properly, and the mouthpiece may not be completely effective in cooperation with the cartridge to convert the medication into a mist which is deposited in the proper bronchial area to relieve the asthmatic attack. Often there are small droplets, rather than a mist, and this may be compounded by improper inhalation which results in much of the medication simply going into the throat and stomach where it is ineffective against the asthmatic attack.

The Inhalation Valve disclosed and claimed in our prior application Ser. No. 359,679 has done an admirable job in breaking up droplets into a mist form and in aiding asthmatic patients to inhale properly, and it has met with considerable commercial success.

OBJECTS AND SUMMARY OF THE INVENTION

In accordance with the present invention a valved chamber is provided for cooperation with a pressurized cannister or cartridge of suitable asthmatic medication which aids the asthmatic sufferer in inhaling properly, and which is highly efficient in breaking up droplets into a mist form.

Accordingly, the principle object of the present invention is to provide a valved air chamber for converting epinephrine or other bronchodilater into a proper mist and insuring substantially complete inhalation thereof by a person suffering an asthmatic attack.

It is a further object of the present invention to provide a valved chamber as noted just above which is directly cooperable with a pressurized canister of bronchodilater material and which is provided with means adjacent the valve of such canister to provide an improved dispersion of droplets and mist therefrom.

Yet another object of the present invention is to provide a vertical chamber having a pressurized container of bronchodilater at the top thereof and discharging down vertically into the chamber wherein a valve is provided at the bottom of the chamber in functional cooperation with a horizontal inhalation valve and mouthpiece at the upper end of the chamber for nebulizing the bronchodilater material and facilitating inhalation thereof by a patient.

In carrying out the foregoing and other objects and advantages of the present invention we provide a cylindrical chamber having a vertical axis and of a proper size to be held conveniently in the hand. An extension cylinder at the top supports a pressurized canister of bronchodilater medication which upon manual depression dispenses a measured dose of medication. A diffuser is provided beneath the valve of the canister for improved dispersion of the medication, thus to form very small droplets and mist within the chamber. A one way valve is provided at the bottom of the chamber to prevent exiting of the medication from the bottom, but to permit entrance of ambient air upon inhalation. A horizontally disposed mouthpiece and one way valve are disposed adjacent the upper margin of the chamber. Following a short time delay after operation of the canister for discharge of medication the patient inhales through this mouthpiece, and both one way valves open, admitting air at the bottom of the chamber as the mist is withdrawn through the horizontal mouthpiece. A reversal of flow and a swirling action are produced which effect a particularly efficient misting of the medication.

DRAWING DESCRIPTION

The present invention will best be understood with reference to the following specification when taken in connection with the accompanying drawings wherein:

FIG. 1 comprises a vertical section through a metered dose inhaler constructed in accordance with the present invention;

FIG. 2 comprises a top view thereof;

FIG. 3 comprises an enlarged view in longitudinal section of the deflector provided in cooperation with the discharge valve of the pressurized medicine container;

DETAILED DESCRIPTION OF THE ILLUSTRATED EMBODIMENT

Figure 1:
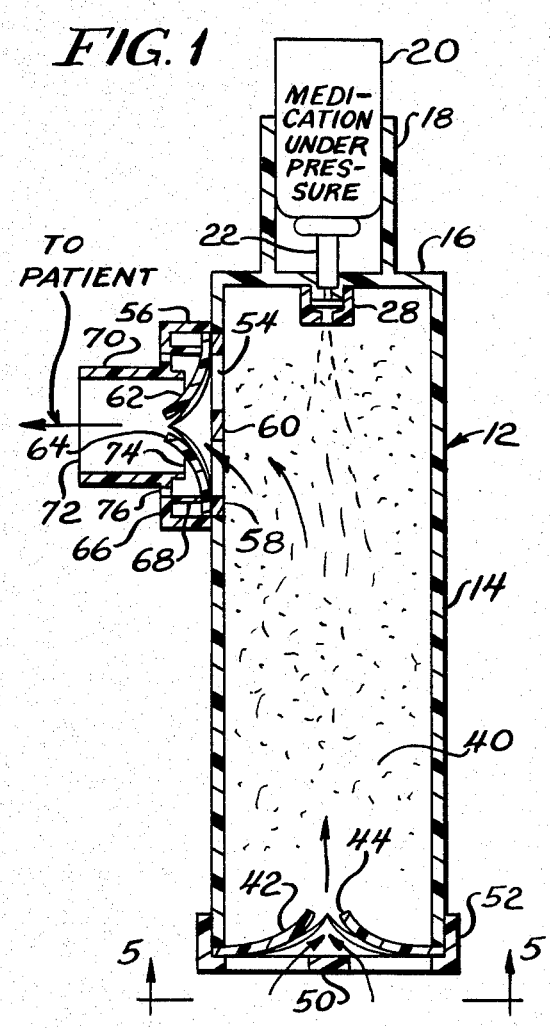
Figure 2:
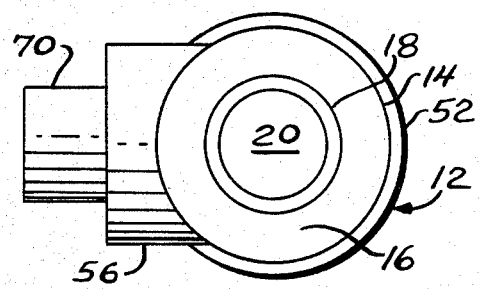
Figure 3:
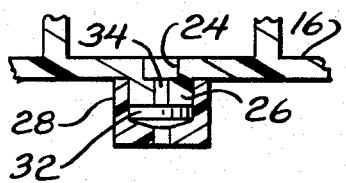

Referring first to FIG. 1, there will be seen a metered dose inhaler constructed in accordance with the present invention and including a molded plastic air chamber 12 of upright cylindrical construction of proper size and shape to fit a human hand and having a cylindrical sidewall 14 and an integral transverse top wall 16. A smaller cylindrical wall 18 extends upwardly from the top wall 16, being integral therewith, and receives a commercially available canister 20 containing asthmatic medication under pressure. The canister or cartridge 20 normally is in raised position within the cylindrical wall 18, as illustrated in FIG. 1, and is provided with a vertically downwardly extending nozzle 22 received in a recess 24 (see also FIG. 3) in the end wall 16. The recess 24 is accompanied by a downwardly extending cylindrical protuberance 26 integral with the transverse upper wall 16, and surrounded by a hollow nipple 28, having an axial bore or aperture 30 therein. A rigid disc shaped diffuser element 32 is disposed within the nipple 28 between a bore 34 in the protuberance 26 and the bore or aperture 30. This diffuser element may be of a porous plastic material, or other porous material, whereby a measured dose of liquid medication dispensed through the valve 22 upon depression of the canister 20 as by the thumb or a finger is diffused, thereby to form mainly a mist rather than droplets exiting through the orifice 30.

Figure 4:
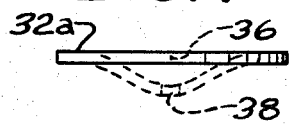
FIG. 4 is a view similar to FIG. 3 showing the modification.
Figure 5:
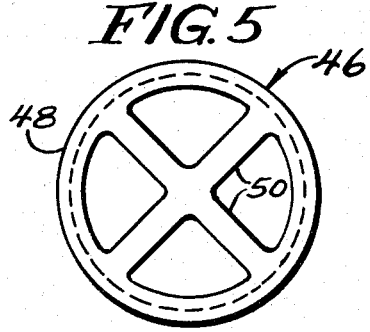
FIG. 5 is an upwardly vertical view taken at the bottom of the chamber substantially along the line 5—5 in FIG. 1.
Figure 6:
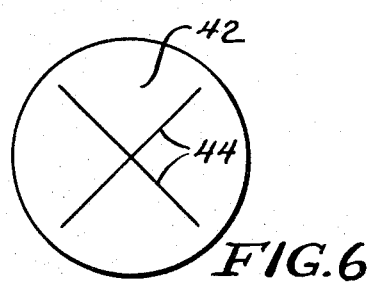
FIG. 6 is a plan view of the valve diaphragm.

A modification of the invention is shown in FIG. 4 wherein the rigid diffuser disc 32 is supplanted by an elastomeric or other resilient flexible disc 32A, shown on an enlarged scale. This disc may be of rubber or suitable flexible plastic material, and is provided with a central puncture 36 which is closed when the disc is in a planar state, but which opens to form an orifice 38 when pressure is applied to the disc to distend it as shown in broken lines in FIG. 4. This structure also helps in nebulizing the medication to form a mist rather than droplets, and might not require cleaning as often as the rigid porous or foraminous disc 32.

In any event, mist from the canister 20 extends down into the air chamber 14 as indicated at 40. The bottom of the air chamber is open as a part of the molding process, and is closed by an elastomeric diaphragm 42 having a pair of diametral slits 44 therein at right angles to one another. A single slit would suffice, but there is improved flexibility with two slits. A spider 46 underlies the diaphgram, comprising an outer circular flange 48 and at least two diametral ribs 50 arranged to underlie the slits 44. An upstanding cylindrical flange 52 about the periphery of the circular flange 48 embraces the bottom portion of the sidewall of the air chamber and is suitable secured thereto, as by sonic or solvent welding.

The diaphragm normally lies flat against the spider 46 with the ribs 50 underlying the slits 44. Thus, the mist 40 cannot exit from the bottom end of the air chamber. However, when the patient inhales as will be brought out shortly hereinafter there is a negative pressure applied to the contents of the air chamber. This causes the diaphragm to deflect upwardly as indicated in FIG. 1, allowing air to enter the air chamber from the bottom so that the mist may be inhaled by the patient.

Figure 7:
FIG. 7 is an enlarged vertical sectional view through a modified construction at the bottom of the chamber.

A modification is shown in FIG. 7 wherein the diaphragm 42 is replaced by a porous or foraminous sheet or diaphragm 42A which has no slots therein. This comprises a sintered porous sheet of polyethylene having pores therein on the order of 500 microns. This is sufficient to allow some air in the air chamber 12 to exit the chamber while retaining mist therein. Any mist that is deposited on the foraminous disc is then picked up by entering air upon patient inhalation for further dispersion as mist.

The cylindrical wall 14 is provided near the upper end thereof with a lateral opening 54 which is surrounded by a molded plastic cylindrical wall 56 secured to the sidewall 14 by suitable means such as adhesive, or solvent or sonic welding. A spider 58 having at least one cross bar 60 is secured across the opening 54 by suitable means, again including adhesive, or solvent or sonic welding. This spider backs up a diaphragm 62 having at least one slit 64 therein, each such slit being backed up by a cross bar or rib 60. The spider and diaphragm are similar to the spider 46 and diaphragm 42 at the bottom of the air chamber.

The cylinder 56 is provided with a transverse wall 66 which has an inwardly directed cylindrical flange 68 pressing against the diaphragm 62 to hold it against the outer portion of the spider 58. A mouthpipe 70 is molded integrally with the transverse wall 66, and is of cylindrical construction having an outer open end 72. The inner end 74 also is open and is spaced from the diaphragm 62 when the parts are at rest. A plurality of air passages 76 is provided in the transverse wall 66 about the mouthpipe 70 and inwardly of the cylindrical flange 68.

It is intended that the mouthpipe 70 should be placed in the patient's mouth, and that the patient should breathe therethrough. He can both inhale and exhale through the mouthpipe, and thus does not require any specific or special breathing techniques as are usually necessary for inhaling the asthmatic medication. Upon exhalation the diaphragm 62 is simply pressed flat against the spider 58 including the rib 60 thereof, and air passes around the inner end 74 of the mouthpipe and out through the apertures 76. On inhalation, the diaphragm flexes outwardly as shown in FIG. 1 and seals against the inner end 74 of the mouthpipe so that the apertures 76 are closed out, and no ambient air can enter the patient's airway. At this time the diaphragm 42 at the bottom of the air chamber flexes up, and the mist 40 in the air chamber is inhaled into the patient's lungs and bronchii where it is most effective.

The downward and then upward flow of the mist in the air chamber provides a particularly good evaporation of any droplets into mist. Movement through the disc 32 or the disc 32A initially brings about a good misting, and further misting is produced by deposition of any droplets that might form on the inside of the sidewall 14 of the air chamber, or on the bottom diaphragm 42, from whence they are evaporated by the patient's inhalation. Since air can enter the air chamber remotely of the mouthpipe upon inhalation by the patient, substantially all of the mist in the air chamber passes into the patient's air passageways. Thus, the medication reaches the patient efficiently both from the standpoint of quantity, in that substantially all of the medication reaches him, and from the standpoint of quality, in that the best possible mist is generated, whereby to be of best use to the patient.

The specific examples of the invention as herein shown and described are for illustrative purposes. Various changes in stucture will no doubt occur to those skilled in the art, and will be understood as forming a part of the present invention insofar as they fall within the spirit and scope of the appended claims.

The invention is claimed as follows:

1. A metered dose inhaler for administering asthmatic medication comprising an upright cylindrical air chamber adapted to be held in the hand, said air chamber having an upper end and a lower end, means adjacent said upper end for supporting a pressurized cartridge of asthmatic medication, means for establishing fluid communication from said cartridge into said air chamber adjacent the upper end thereof for spraying a measured dose of medication into said air chamber, a one way valve adjacent the lower end of said air chamber for admitting air but retaining medication, a mouthpipe disposed laterally of said air chamber adjacent the upper end thereof for receipt in a patient's mouth, said air chamber opening into said mouthpipe, and one way valve means between said air chamber and said mouthpipe to pass misted medication from said air chamber through said mouthpipe and into said patient upon patient inhalation and to preclude entrance of air through said mouthpipe into said air chamber upon patient exhalation, said one way valve means having bypass means for venting exhaled air to atmosphere.

2. An inhaler as set forth in claim 1 wherein the means for supporting the pressurized cartridge comprises a cylindrical wall upstanding from the upper end of said air chamber.

3. An inhaler as set forth in claim 1 wherein the means for establishing fluid communication includes a diffuser for said spray.

4. An inhaler as set forth in claim 3 wherein the diffuser comprises a porous element through which the medication passes.

5. An inhaler as set forth in claim 3 wherein the diffuser comprises a flexible, resilient diaphragm having a normally closed aperture therein, said diaphragm deflecting upon pressurized dispensation of medication to open said aperture.

6. An inhaler as set forth in claim 1 wherein the one way valve at the lower end of the air chamber comprises a flexible, resilient diaphragm having at least one slit therein, and a member underlying said diaphragm and having a portion backing said slit to prevent exiting of mist through said slit, said diaphragm flexing upwardly and opening said slit upon inhalation.

7. An inhaler as set forth in claim 6 wherein said one way valve at the bottom of said air chamber comprises a porous disc.

8. An inhaler as set forth in claim 1 wherein the one way valve means between the air chamber and the mouthpipe comprises a flexible, resilient diaphragm having at least one slit therein, and a member disposed between said diaphragm and said air chamber and having a portion backing said slit to prevent entrance of air into said air chamber upon exhalation, said diaphragm flexing and said slit opening upon inhalation.

9. An inhaler as set forth in claim 8 wherein said mouthpipe has a cylindrical extension confronting said diaphragm and spaced therefrom with said diaphragm in relaxed condition, and means providing bypass means disposed radially outwardly of said mouthpipe extension, said diaphragm flexing upon inhalation into engagement with said mouthpipe extension and sealing said exhaust means from said mouthpipe.

* * * * *